(12) United States Patent
Harmer et al.

(10) Patent No.: US 7,157,588 B2
(45) Date of Patent: Jan. 2, 2007

(54) IONIC LIQUIDS

(75) Inventors: Mark Andrew Harmer, Kennett Square, PA (US); Christopher P. Junk, Wilmington, DE (US); Leo Ernest Manzer, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 13 days.

(21) Appl. No.: 11/107,440

(22) Filed: Apr. 15, 2005

(65) Prior Publication Data

US 2006/0235230 A1    Oct. 19, 2006

(51) Int. Cl.
*C07D 207/12* (2006.01)
*A61K 31/4015* (2006.01)

(52) U.S. Cl. .................... 548/543; 548/543; 252/364
(58) Field of Classification Search ............. 548/543; 252/364
See application file for complete search history.

(56) References Cited

U.S. PATENT DOCUMENTS 6,818,593 B1 * 11/2004 Manzer ................. 504/283

OTHER PUBLICATIONS

Robin D. Rogers et al., "Ionic Liquids—Solvents of the Future?", Science, Oct. 31, 2003, pp. 792-793, vol 302, www.sciencemag.org.
D. Demberelnyamba et al., "Ionic liquids based on N-vinyl-γ-butyrolactam: potential liquid electrolytes and green solvents", Chem. Commun., 2002, pp. 1538-1539, www.rsc.org/chemcomm.

* cited by examiner

*Primary Examiner*—Kamal A. Saeed
*Assistant Examiner*—Janet L. Coppins
(74) *Attorney, Agent, or Firm*—Gerald E. Deitch

(57) ABSTRACT

The present invention relates to compositions of matter that are useful as ionic liquids. The compositions of the invention are based on an N-substituted pyrrolidinone, said pyrrolidinone having a pendant ammonium cation that is separated from the pyrrolidone ring by a variable length alkyl spacer.

4 Claims, No Drawings

IONIC LIQUIDS

FIELD OF INVENTION

This invention relates to compositions of matter that are useful as ionic liquids.

BACKGROUND OF THE INVENTION

Ionic liquids are liquids composed of ions that are fluid around or below 100 degrees C. (Science (2003) 302: 792–793). Ionic liquids exhibit negligible vapor pressure, and with increasing regulatory pressure to limit the use of traditional industrial solvents due to environmental considerations such as volatile emissions and aquifer and drinking water contamination, much research has been devoted to designing ionic liquids that could function as replacements for conventional solvents.

Ionic liquids generally consist of salts of organic cations, such as the N-alkylpyridinium, 1,3-dialkylimidazolium, tetraalkylammonium, tetraalkylphosphonium and trialkylsulfonium cations. Demberelnyamba, Shin and Lee (Chem. Commun. (2002) 1538–1539) describe petroleum-derived ionic liquids based on N-vinyl-γ-butyrolactam having the Formula:

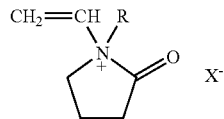

wherein X⁻ is a bromide or tetrafluoroborate anion.

Described herein are novel compositions based on pyrrolidinones that are useful as ionic liquids. The compositions of the present invention exhibit unique properties due to separation of the ammonium cation from the pyrrolidinone ring using a variable-length alkyl spacer group.

SUMMARY OF THE INVENTION

The present invention relates to a composition of matter of the Formula:

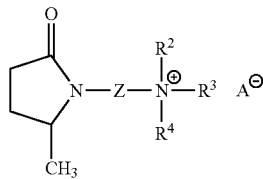

wherein:
(i) Z is —(CH$_2$)$_n$—, wherein n is an integer from 2 to 12;
(ii) R$^2$, R$^3$ and R$^4$ taken independently are H, —CH$_3$, —CH$_2$CH$_3$ or C$_3$ to C$_6$ straight-chain or branched monovalent alkyl; and
(iii) A⁻ is an anion selected from the group consisting of [BF$_4$]⁻, [PF$_6$]⁻, [SbF$_6$]⁻, [CH$_3$CO$_2$]⁻, [HSO$_4$]⁻, [CF$_3$SO$_3$]⁻, [HCF$_2$CF$_2$SO$_3$]⁻, [CF$_3$HFCCF$_2$SO$_3$]⁻, [HCClFCF$_2$SO$_3$]⁻, [(CF$_3$SO$_2$)$_2$N]⁻, [AlCl$_4$]⁻, [CF$_3$CO$_2$]⁻, [NO$_3$]⁻, [SO$_4$]$^{2-}$, Cl⁻, Br⁻, I⁻, and F⁻.

In one embodiment of the invention, Z is —(CH$_2$)$_n$—, wherein n is an integer from 2 to 6. In another embodiment of the invention, the anion is [PF$_6$]⁻, [HCF$_2$CF$_2$SO$_3$]⁻, [CF$_3$HFCCF$_2$SO$_3$]⁻, [HCClFCF$_2$SO$_3$]⁻ or [(CF$_3$SO$_2$)$_2$N]⁻.

DETAILED DESCRIPTION OF THE INVENTION

The present invention relates to novel compositions based on N-substituted pyrrolidinones, said pyrrolidinones having a pendant ammonium cation that is separated from the pyrrolidone ring by a variable length alkyl spacer. Compositions of the invention should be useful as solvents and, perhaps, as catalysts for many reactions, including aromatic electrophilic substitution, nitration, acylation, esterification, etherification, oligomerization, transesterification, isomerization and hydration. Use of pyrrolidinone-based compositions of the present invention is also advantageous because the pyrrolidinones can be readily prepared from levulinic acid or levulinic acid derivatives obtained from the hydrolysis of inexpensive renewable biomass feedstock.

Definitions

In this disclosure, a number of terms and abbreviations are used. The following definitions are provided.

By "ionic liquids" is meant organic salts that are fluid around or below 100 degrees C.

By "alkyl" is meant a monovalent radical having the general Formula C$_n$H$_{2n+1}$. "Monovalent" means having a valence of one.

By "hydrocarbyl" is meant a monovalent group containing only carbon and hydrogen.

By "catalyst" is meant a substance that affects the rate of the reaction but not the reaction equilibrium, and emerges from the process chemically unchanged.

By "homogeneous acid catalyst" is meant a catalyst that is molecularly dispersed with the reactants in the same phase.

By "metal catalyst" is meant a catalyst that is comprised of at least one metal, at least one Raney® metal, compounds thereof or combinations thereof.

By "promoter" is meant an element of the Periodic Table that is added to enhance the physical or chemical function of the catalyst. The promoter can also be added to retard undesirable side reactions and/or affect the rate of the reaction.

By "metal promoter" is meant a metallic compound that is added to enhance the physical or chemical function of a catalyst. The metal promoter can also be added to retard undesirable side reactions and/or affect the rate of the reaction.

"Selectivity" refers to the weight percent of a particular reaction product in the total product weight (including the weight of unreacted reactants).

"Conversion" refers to the weight percent of a particular reactant that is converted to product.

The term "pyrrolidinone" is used synonymously with "pyrrolidone"; the term "pyrrolidine-2-one" is used synonymously with "2-pyrrolidone".

As used herein, the term "biomass" refers to any cellulosic or lignocellulosic material and includes materials comprising cellulose, and optionally further comprising hemicellulose, lignin, starch, oligosaccharides and/or monosaccharides. Biomass may also comprise additional components, such as protein and/or lipid. According to the invention, biomass may be derived from a single source, or biomass can comprise a mixture derived from more than one source. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, wheat straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers and animal manure.

The present invention relates to compositions of matter of the Formula:

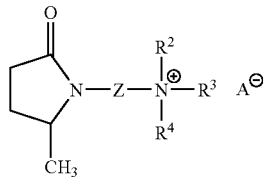

wherein:
(i) Z is $-(CH_2)_n-$, wherein n is an integer from 2 to 12;
(ii) $R^2$, $R^3$ and $R^4$ taken independently are H, $-CH_3$, $-CH_2CH_3$ or $C_3$ to $C_6$ straight-chain or branched monovalent alkyl; and
(iii) $A^-$ is an anion selected from the group consisting of $[BF_4]^-$, $[PF_6]^-$, $[SbF_6]^-$, $[CH_3CO_2]^-$, $[HSO_4]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[AlCl_4]^-$, $[CF_3CO_2]^-$, $[NO_3]^-$, $[SO_4]^{2-}$, $Cl^-$, $Br^-$, $I^-$, and $F^-$.

In one embodiment of the invention, Z is $-(CH_2)_n-$, wherein n is an integer from 2 to 6. In another embodiment of the invention, the anion is selected from the group consisting of $[PF_6]^-$, $[HCF_2CF_2SO_3]^-$, $[CF_3HFCCF_2SO_3]^-$, $[HCClFCF_2SO_3]^-$ and $[(CF_3SO_2)_2N]^-$. In still another embodiment, Z is $-(CH_2)_n-$, wherein n is an integer from 2 to 6, and the anion is selected from the group consisting of $[PF_6]^-$, $[HCF_2CF_2SO_3]^-$, $[CF_3HFCCF_2SO_3]^-$, $[HCClFCF_2SO_3]^-$ and $[(CF_3SO_2)_2N]^-$.

The composition may be synthesized from a pyrrolidine-2-one of the Formula:

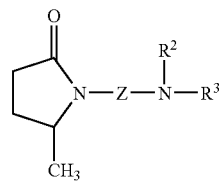

wherein:
(i) Z is $-(CH_2)_n-$, wherein n is an integer from 2 to 12; and
(ii) $R^2$ and $R^3$ taken independently are H, $-CH_3$, $-CH_2CH_3$ or $C_3$ to $C_6$ straight-chain or branched monovalent alkyl.

Synthesis of N-hydrocarbyl Pyrrolidine-2-one:

The pyrrolidine-2-one may be synthesized by contacting levulinic acid or an ester thereof with a diamine of the Formula $R^2R^3N$-Z-$NH_2$ in the presence of hydrogen gas and a catalyst according to Reaction (I):

Reaction (I)

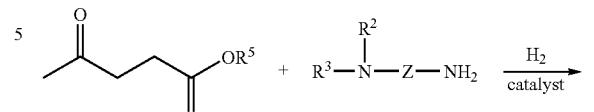

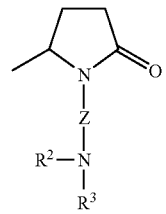

wherein:
(i) Z is $-(CH_2)_n-$, wherein n is an integer from 2 to 12;
(ii) $R^2$ and $R^3$ taken independently are H, $-CH_3$, $-CH_2CH_3$ or $C_3$ to $C_6$ straight-chain or branched monovalent alkyl; and
(iii) $R^5$ is H, $-CH_3$, $-CH_2CH_3$ or $C_3$ to $C_8$ straight-chain or branched monovalent alkyl.

In another embodiment, the pyrrolidine-2-one may be synthesized by contacting a salt of levulinic acid, such as ammonium levulinate, with a diamine of the Formula $R^2R^3N$-Z-$NH_2$ in the presence of hydrogen gas and a catalyst.

In one embodiment of the invention, Z is $-(CH_2)_n-$, wherein n is an integer from 2 to 6. In another embodiment, $R^5$ is ethyl.

The pyrrolidine-2-one formed in Reaction (I) can be synthesized according to the methods and conditions taught in U.S. Pat. No. 6,818,593 (hereinafter to referred to as '593). Although '593 describes the synthesis of 5-methyl-N-alkyl-2-pyrrolidinone from the reductive amination of levulinic acid with nitro compounds, the methods and conditions taught in '593 (column 2, line 66 through column 7, line 21) can be utilized for the process described by Reaction (I) wherein levulinic acid, a salt thereof, or an ester thereof and a diamine are converted to a pyrrolidine-2-one in the presence of hydrogen gas and a catalyst.

Levulinic acid may be obtained from biomass. For the conversion of biomass to levulinic acid, biomass may be contacted with water and an acid catalyst in a train of one or more reactors, preferably under pressure at elevated temperature. This basic process is described, for example, in U.S. Pat. No. 5,608,105, U.S. Pat. No. 5,859,263, U.S. Pat. No. 6,054,611 and U.S. Patent Application 2003/0233011. Generally, cellulose in the biomass is converted to levulinic acid and formate in one or more reactors. Levulinic acid produced from biomass may also be converted to levulinic acid esters for example as described in U.S. 2003/0233011A1 through the reaction of levulinic acid with olefins.

For the synthesis of pyrrolidine-2-ones according to Reaction (I), a molar ratio of diamine to levulinic acid, a salt thereof, or an ester thereof of from about 0.01/1 to about 100/1 is preferred at the start of the reaction; a molar ratio of about 0.3/1 to about 5/1 is further preferred at the start of the reaction. A temperature range of from about 25 degrees C. to about 300 degrees C. is used for the reductive amination reaction; a temperature range of from about 75 degrees C. to about 200 degrees C. is preferred. A pressure range of from about 0.3 MPa to about 20.0 MPa is employed for the reaction; a pressure range of from about 1.3 MPa to about 7.6 MPa is preferred. The reaction may be performed in a non-reacting solvent medium such as water, alcohols, ethers, and pyrrolidones. Alternatively, the excess of diamine can also act as the medium of the reaction.

The principal component of the catalyst useful for Reaction (I) is selected from metals from the group consisting of palladium, ruthenium, rhenium, rhodium, iridium, platinum, nickel, cobalt, copper, iron, osmium; compounds thereof; and combinations thereof.

A chemical promoter may augment the activity of a catalyst. The promoter may be incorporated into the catalyst during any step in the chemical processing of the catalyst constituent. The chemical promoter generally enhances the physical or chemical function of the catalyst agent, but can also be added to retard undesirable side reactions. Suitable promoters for the processes of the invention include metals selected from tin, zinc, copper, gold, silver, and combinations thereof. The preferred metal promoter is tin. Other promoters that can be used are elements selected from Group 1 and Group 2 of the Periodic Table.

The catalyst may be supported or unsupported. A supported catalyst is one in which the active catalyst agent is deposited on a support material by a number of methods, such as spraying, soaking or physical mixing, followed by drying, calcination, and if necessary, activation through methods such as reduction or oxidation. Materials frequently used as a support are porous solids with high total surface areas (external and internal) which can provide high concentrations of active sites per unit weight of catalyst. The catalyst support may enhance the function of the catalyst agent. A supported metal catalyst is a supported catalyst in which the catalyst agent is a metal.

A catalyst that is not supported on a catalyst support material is an unsupported catalyst. An unsupported catalyst may be platinum black or a Raney® (W.R. Grace & Co., Columbia, Md.) catalyst. Raney® catalysts have a high surface area due to selectively leaching an alloy containing the active metal(s) and a leachable metal (usually aluminum). Raney® catalysts have high activity due to the higher specific area and allow the use of lower temperatures in hydrogenation reactions. The active metals of Raney® catalysts include nickel, copper, cobalt, iron, rhodium, ruthenium, rhenium, osmium, iridium, platinum, palladium; compounds thereof; and combinations thereof.

Promoter metals may also be added to the base Raney® metals to affect selectivity and/or activity of the Raney® catalyst. Promoter metals for Raney® catalysts may be selected from transition metals from Groups IIIA through VIIIA, IB and IIB of the Periodic Table of the Elements. Examples of promoter metals include chromium, molybdenum, platinum, rhodium, ruthenium, osmium, and palladium, typically at about 2% by weight of the total metal.

The catalyst support useful herein can be any solid, inert substance including, but not limited to, oxides such as silica, alumina and titania; barium sulfate; calcium carbonate; and carbons. The catalyst support can be in the form of powder, granules, pellets, or the like.

A preferred support material of the invention is selected from the group consisting of carbon, alumina, silica, silica-alumina, silica-titania, titania, titania-alumina, barium sulfate, calcium carbonate, strontium carbonate, compounds thereof and combinations thereof. Supported metal catalysts can also have supporting materials made from one or more compounds. More preferred supports are carbon, titania and alumina. Further preferred supports are carbons with a surface area greater than 100 $m^2/g$. A further preferred support is carbon with a surface area greater than 200 $m^2/g$. Preferably, the carbon has an ash content that is less than 5% by weight of the catalyst support; the ash content is the inorganic residue (expressed as a percentage of the original weight of the carbon) which remains after incineration of the carbon.

The preferred content of the metal catalyst in the supported catalyst is from about 0.1% to about 20% of the supported catalyst based on metal catalyst weight plus the support weight. A more preferred metal catalyst content range is from about 1% to about 10% of the supported catalyst.

Combinations of metal catalyst and support system may include any one of the metals referred to herein with any of the supports referred to herein. Preferred combinations of metal catalyst and support include palladium on carbon, palladium on calcium carbonate, palladium on barium sulfate, palladium on alumina, palladium on titania, platinum on carbon, platinum on alumina, platinum on silica, iridium on silica, iridium on carbon, iridium on alumina, rhodium on carbon, rhodium on silica, rhodium on alumina, nickel on carbon, nickel on alumina, nickel on silica, rhenium on carbon, rhenium on silica, rhenium on alumina, ruthenium on carbon, ruthenium on alumina and ruthenium on silica.

Further preferred combinations of metal catalyst and support include palladium on carbon, palladium on alumina, palladium on titania, platinum on carbon, platinum on alumina, rhodium on carbon, rhodium on alumina, ruthenium on carbon and ruthenium on alumina.

Suitable diamines for Reaction (I) may be obtained commercially from, for example, Huntsman (Houston, Tex.) or BASF (Mount Olive, N.J.), or may be synthesized by methods well known to those skilled in the art. For a discussion of the synthesis of diamines, see, for example, Eller, K. and Henkes, E., Diamines and Polyamines (Ullmanns Encyclopedia of Industrial Chemistry (2002) Wiley-VCH Verlag GmbH & Co, Chapter 8) and Experimental Methods in Organic Chemistry, $3^{rd}$ Edition (Moore, J., Dalrymple, D. and Rodig, O. (eds.) (1982) Saunders College Publishing, NY, Chapter 22. Suitable diamines are those having the Formula $R^2R^3N-Z-NH_2$ wherein Z is $-(CH_2)_n-$, wherein n is an integer from 2 to 12 and $R^2$ and $R^3$ taken independently are H, $-CH_3$, $-CH_2CH_3$ or $C_3$ to $C_6$ straight-chain or branched monovalent alkyl.

The formation of pyrrolidine-2-ones may be carried out in batch, sequential batch (i.e., a series of batch reactors) or in continuous mode in any of the equipment customarily employed for continuous process (see for example, H. S. Fogler, Elementary Chemical Reaction Engineering, Prentice-Hall, Inc., N.J., USA).

The pyrrolidinones synthesized according to Reaction (I) may be recovered, for example, by distillation, or by filtration to remove solid acid catalyst particles if present.

Conversion of a Pyrrolidine-2-one to a Composition of the Present Invention

A composition of the present invention may be synthesized by quaternizing the non-ring nitrogen of the pyrrolidine-2-one to obtain a quaternary ammonium compound of the Formula:

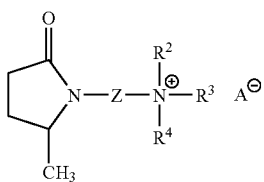

wherein Z is —$(CH_2)_n$— wherein n is an integer from 2 to 12, $R^2$, $R^3$, and $R^4$ taken independently are —$CH_3$, —$CH_2CH_3$ or $C_3$ to $C_6$ straight-chain or branched monovalent alkyl, and A- is selected from the group consisting of $Cl^-$, $Br^-$, and $I^-$.

In order to form a quaternary ammonium compound, the pyrrolidine-2-one is contacted with an alkylating halide having the Formula $R^1$-A wherein $R^1$ is selected from the group consisting of —$CH_3$, —$CH_2CH_3$ or $C_3$ to $C_8$ straight-chain or branched monovalent alkyl, and $A^-$ is selected from the group consisting of $Cl^-$, $Br^-$, and $I^-$. Methods for performing quaternization reactions are well-known and are described in Organic Chemistry (Morrison and Boyd (ed.) 3$^{rd}$ Edition (1973) Allyn and Bacon, Inc., Boston, Chapter 23.5, pages 752–753).

The quaternization reaction may optionally be carried out in an inert solvent, such as acetonitrile, acetone or dichloromethane. The quaternization may be accomplished by refluxing of the reactants, optionally under an inert atmosphere. When the compositions of the present invention and/or the reactants used for synthesis of the compositions are hygroscopic, it is preferable to carry out the quaternization and/or anion exchange reaction (see below) under conditions that exclude water and air. The alkylating halide is present in slight excess (ca. 5%) at the start of the reaction. The reaction is carried out at a temperature of from about 10 degrees C. to about 80 degrees C.; the reaction is preferably carried out at a temperature of from about 30 degrees C. to about 70 degrees C., more preferably from about 60 degrees C. to about 70 degrees C. The time for the reaction is generally from about 1 minute to about 48 hours; the time for the reaction is preferably from about 30 minutes to about 24 hours.

Anion Exchange

The compositions of the present invention are expected to be liquid at room temperature, making it appropriate to refer to them as "ionic liquids." However, if they are not liquid at room temperature it may be possible to convert them to a liquid by substituting a different anion, i.e., $A^-$, by an anion exchange reaction. Thus, the quaternary ammonium composition may be further contacted with $M^+A^-$, wherein M is selected from the group consisting of H, Li, K, Na, Ag, Mg, Ca, Ce, Ba, Rb and Sr, and $A^-$ is an anion selected from the group consisting of $[BF_4]^-$, $[PF_6]^-$, $[SbF_6]^-$, $[CH_3CO_2]^-$, $[HSO_4]^-$, $[NO_3]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[AlCl_4]^-$, $[CF_3CO_2]^-$, $[NO_3]^-$, $[SO_4]^{2-}$, $Cl^-$, $Br^-$, $I^-$ and $F^-$, to form a composition having the desired anion. Prior to the exchange reaction, excess alkylating agent may be removed, for example, by evaporation. In addition, the quaternary ammonium compound may be washed with a solvent and dried prior to the anion exchange reaction. The anion exchange reaction may be carried out by mixing the quaternary ammonium compound with $M^+A^-$, optionally under an inert atmosphere. The anion exchange reaction may be carried out at a temperature of from about –20 degrees C. to about 100 degrees C. for a time of about 1 second to about 72 hours. Solvents useful in the reaction should be inert to the reactants and products, and include methanol, ethanol, acetone and acetonitrile. Choice of the appropriate solvent or mixture of solvents will allow for separation of the composition comprising the desired anion from the composition comprising the less desired anion as is well known in the art and as is shown herein in Example 2(b). Additional techniques may be utilized to enhance the anion exchange reaction, such as ultrasonication as taught in WO 03/048078.

The composition comprising the desired anion can be recovered by a suitable technique such as evaporation of the reaction solvent under reduced pressure, decantation and/or filtration to remove precipitated salts.

Compositions (ionic liquids) of the present invention can be utilized in one phase systems or multiple phase systems as solvents or, perhaps, as catalysts. The physical and chemical properties of the compositions (ionic liquids) of the present invention can be specifically selected by choice of the appropriate cation and anion. For example, increasing the chain length of one or more alkyl chains of the cation will affect properties such as the melting point, hydrophilicity/lipophilicity, density and solvation strength of the ionic liquid. Choice of the anion can affect, for example, the melting point, the water solubility and the acidity and coordination properties of the composition. Thus it may be desirable to perform an anion exchange reaction by contacting the composition with $M^+A^-$ as described above to replace a less desirable anion of an ionic liquid with an anion that gives the desired chemical and physical properties for the ionic liquid composition. Effects of cation and anion on the physical and chemical properties of ionic liquids are known to those skilled in the art and are reviewed in detail by Wassersheid and Keim (Angew. Chem. Int. Ed, supra) and Sheldon (Chem. Commun., supra).

Alkylation of Aromatic Compounds with Monoolefins

In one embodiment of the present invention, compositions of the invention are useful as solvents for the production of at least one alkylated aromatic compound of the Formula:

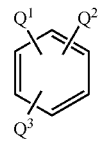

wherein:
 a) $Q^1$ is H, —$CH_3$, —$C_2H_5$, or $CH_3$—CH—$CH_3$;
 b) $Q^2$ is H, —$CH_3$ or —$C_2H_5$; and
 c) $Q^3$ is —$C_2H_5$ or $C_3$ to $C_{18}$ straight chain alkyl group having therein a single CH group, the carbon atom of which is bonded to the aromatic compound.

In one embodiment of the invention, $Q^1$ and $Q^2$ are both H.

Alkylated aromatic compounds have many industrial uses, including as intermediates in styrene production, cumene production and surfactant synthesis.

The production of at least one alkylated aromatic compound is carried out by a process comprising:

(1) reacting a $C_2$ to $C_{18}$ straight-chain monoolefin with an aromatic compound of the Formula:

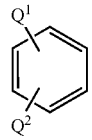

wherein $Q^1$ and $Q^2$ are as defined above;

in an ionic liquid of the Formula:

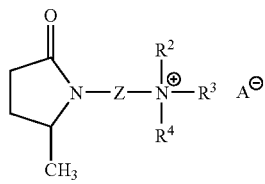

wherein:

(i) Z is —$(CH_2)_n$—, wherein n is an integer from 2 to 12;
(ii) $R^2$, $R^3$ and $R^4$ taken independently are H, —$CH_3$, —$CH_2CH_3$ or $C_3$ to $C_6$ straight-chain or branched monovalent alkyl; and
(iv) $A^-$ is an anion selected from the group consisting of $[BF_4]^-$, $[PF_6]^-$, $[SbF_6]^-$, $[CH_3CO_2]^-$, $[HSO_4]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[AlCl_4]^-$, $[CF_3CO_2]^-$, $[NO_3]^-$, $[SO_4]^{2-}$, $Cl^-$, $Br^-$, $I^-$, and $F^-$;

in the presence of an acid catalyst that is soluble in the ionic liquid, and (2) separating the organic phase comprising the at least one alkylated aromatic compound from the ionic liquid phase.

The alkylation reaction yields a mixture of products. Thus, the organic phase of step (2) comprises a product mixture comprising at least one alkylated aromatic compound of the Formula:

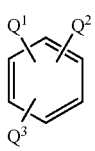

wherein $Q^1$, $Q^2$ and $Q^3$ are as defined above.

The acid catalyst is a homogeneous acid catalyst such as $CF_3SO_3H$, $HCF_2CF_2SO_3H$, $AlCl_3$, HF, $H_2SO_4$, $H_3PO_4$ or HCl. The acid catalyst is used at a concentration from about 0.01% to about 10% by weight of the reaction solution comprising the aromatic compound, the monoolefin and the ionic liquid.

The aromatic compound is benzene or a benzene-derivative, such as toluene, xylene, ethyl benzene or isopropyl benzene.

The ionic liquid comprises from about 1% to about 75% by weight of the reaction solution.

The reaction is carried out at a temperature between about 25 degrees C. and about 200 degrees C., and a pressure between atmospheric pressure and that pressure required to maintain the reactants in a liquid state. In one embodiment of the invention, the reaction is carried out at about 25 degrees C. at pressure is atmospheric pressure.

At the start of the reaction the aromatic compound is in molar excess relative to the monoolefin. In one embodiment, the molar ratio of the aromatic compound to the monoolefin at the start of the reaction is about 8:1.

An advantage to the use of an ionic liquid in this reaction is that the reaction product comprises an organic phase that comprises the at least one alkyl aromatic compound and an ionic liquid phase that comprises the acid catalyst. Thus the at least one alkyl aromatic compound in the organic phase is easily recoverable from the acid catalyst by, for example, decantation. The acid catalyst in the ionic liquid may be recycled and used in subsequent reactions.

The aromatic alkylation reaction may be carried out in batch, sequential batch (i.e., a series of batch reactors) or in continuous mode in any of the equipment customarily employed for continuous process (see for example, H. S. Fogler, Elementary Chemical Reaction Engineering, Prentice-Hall, Inc., N.J., USA). One skilled in the art will recognize that at higher temperatures or pressures a sealed vessel or pressure vessel is required.

EXAMPLES

The following abbreviations are used:

Nuclear magnetic resonance is abbreviated NMR; thermogravimetric analysis is abbreviated TGA, gas chromatography is abbreviated GC; gas chromatography-mass spectrometry is abbreviated GC-MS; thin layer chromatography is abbreviated TLC. Centigrade is abbreviated C, mega Pascal is abbreviated MPa, gram is abbreviated "g", milliliter is abbreviated "ml", hour is abbreviated "hr".

ESCAT-142 (Pd/C catalyst) was obtained from Engelhard Corp. (Iselin, N.J.). Ethyl levulinate and N,N-dimethylethylenediamine were obtained from Alfa Aesar (Ward Hill, Mass.). Acetonitrile, iodopropane, bromopropane, bromopentane, ethanol, sodium hydroxide, triflic acid, potassium triflate, 1-dodecene, p-xylene, bis-trifluoromethanesulfonimide, and bis-hexafluorophosphate were obtained from Sigma-Aldrich (St. Louis, Mo.).

Example 1

Preparation of the Bis-Trifluoromethanesulfonimide Salt of 1-(2-N,N-Dimethylpropylaminoethyl)-5-Methyl-Pyrrolidine-2-one a) Preparation of 1-(2-N,N-Dimethylaminoethyl)-5-Methyl-Pyrrolidine-2-one Ethyl levulinate (18.5 g), N,N-dimethylethylenediamine (11.3 g), and 5% Pd/C (ESCAT-142, 1.0 g) were mixed in a 400 ml shaker tube reactor. The reaction was carried out at 150 degrees C. for 8 hr under 6.9 MPa of $H_2$.

The reactants and products were analyzed by gas chromatography on a HP-6890 GC (Agilent Technologies; Palo Alto, Calif.) and HP-5972A GC-MS detector equipped with a 25 M×0.25 MM ID CP-Wax 58 (FFAP) column. The GC yields were obtained by adding methoxyethyl ether as the internal standard. The ethyl levulinate conversion was 99.7%, and the product selectivity for 1-(2-N,N-dimethylaminoethyl)-5-methyl-pyrrolidine-2-one was 98.6%.

b) Preparation of the Iodide Salt of 1-(2-N,N,N-Dimethylpropylaminoethyl)-5-Methyl-Pyrrolidine-2-one For the quaternization reaction, purified 1-(2-N,N-dimethylaminoethyl)-5-methyl-pyrrolidine-2-one (1.7 g) was placed in 5 g of dry acetonitrile, and 1.69 g of 1-iodopropane was added. This mixture was refluxed overnight under a nitrogen atmosphere; the reaction was shown to be complete via TLC, yielding the iodide salt of the quaternary ammonium compound. The acetonitrile was then removed under vacuum.

c) Preparation of the Bis-Trifluoromethanesulfonimide Salt of 1-(2-N,N,N-Dimethylpropylaminoethyl)-5-Methyl-Pyrrolidine-2-one by Anion Exchange For the anion exchange reaction, the iodide salt (1 g) produced in the quaternization reaction of step (b) was added to water (5 g), and then ethanol (5 g) was added. A stoichiometric amount of bis-trifluoromethanesulfonimide was added and the mixture was stirred for about 24 hours under nitrogen. A separate layer formed at the bottom, orange-red in color, which was quickly washed with water; the upper layer was decanted. The orange-red liquid was then placed in an oven at 100 degrees C. under vacuum for 48 hours to obtain the ionic liquid (bis-trifluoromethanesulfonimide salt of 1-(2-N,N,N-dimethylpropylaminoethyl)-5-methyl-pyrrolidine-2-one). The stability of the ionic liquid was investigated by thermogravimetric analysis as follows: the ionic liquid (79 mg) was heated at 10 degrees C. per minute up to 800 degrees C. using a Universal V3.9A TA instrument analyser (TA Instruments, Inc., Newcastle, Del.); the results demonstrated that the ionic liquid is stable to decomposition up to about 300 degrees C.

Example 2

Preparation of the Hexafluorophosphate Salt of 1-(2-N,N,N-Dimethylpropylaminoethyl)-5-Methyl-Pyrrolidine-2-one a) Preparation of the Bromide Salt of 1-(2-N,N,N-Dimethylpropylaminoethyl)-5-Methyl-Pyrrolidine-2-one For the quaternization reaction purified 1-(2-N,N-dimethylaminoethyl)-5-methyl-pyrrolidine-2-one (1 g) synthesized in Example 1 was placed in 5 g of dry acetonitrile, and 0.71 g of 1-bromopropane was added. This mixture was refluxed overnight under a nitrogen atmosphere; the reaction was shown to be complete via TLC, yielding the bromide salt of the quaternary ammonium compound. The acetonitrile was then removed under vacuum.

b) Preparation of the Hexafluorophosphate Salt of 1-(2-N,N,N-Dimethylpropylaminoethyl)-5-Methyl-Pyrrolidine-2-one by Anion Exchange For the anion exchange reaction, the bromide salt (0.5 g) produced in the quaternization reaction of Example 2(a) was added to water (5 g), and then ethanol (5 g) was added. A stoichiometric amount of bis-hexafluorophosphate (Sigma-Aldrich) was added, followed by an additional 2 ml of water, and the mixture was stirred for about 24 hours under nitrogen. A separate layer formed at the bottom, which was quickly washed with water; the upper layer was decanted. The remaining liquid was then placed in an oven at 100 degrees C. under vacuum for 48 hours to obtain the ionic liquid; 0.6 g of the ionic liquid was obtained.

Example 3

Preparation of the Bromide Salt of 1-(2-N,N,N-Dimethylpentylaminoethyl)-5-Methyl-Pyrrolidine-2-one a) Preparation of the Bromide Salt of 1-(2-N,N,N-Dimethylpentylaminoethyl)-5-Methyl-Pyrrolidine-2-one For the quaternization reaction purified 1-(2-N,N-dimethylaminoethyl)-5-methyl-pyrrolidine-2-one (1 g) synthesized in Example 1(a) was placed in 5 g of dry acetonitrile, and 1.51 g of 1-bromopentane was added. This mixture was refluxed overnight under a nitrogen atmosphere; the reaction was shown to be complete via TLC, yielding the bromide salt of the quaternary ammonium compound. The acetonitrile was then removed under vacuum, yielding the ionic liquid.

b) Preparation of the Trifluoromethylsulfonate Salt of 1-(2-N,N,N-Dimethylpentylaminoethyl)-5-Methyl-Pyrrolidine-2-one For the quaternization reaction, purified 1-(2-N,N-dimethylaminoethyl)-5-methyl-pyrrolidine-2-one (13.5 g) from step (a) was placed in 20 g of dry acetonitrile, and 10 g of 1-bromopropane was added. The mixture was heated at 60 degrees C. for 4 hours. Potassium triflate was then added in acetonitrile (9.5 g in 30 ml of acetonitrile). The mixture was stirred for 4 hours at 60 degrees C. and then left overnight at room temperature. The potassium bromide precipitated. The mixture was filtered and the potassium bromide-free solid was placed under vacuum to remove the solvent. The mixture was dried to give the trifluoromethanesulfonate as the anion of the ionic liquid. The product was confirmed by NMR. The final yield of the ionic liquid (trifluoromethylsulfonate salt of 1-(2-N,N,N-dimethylpentylaminoethyl)-5-methyl-pyrrolidine-2-one) was 13 g.

Example 4

Alkylation of Xylene with Dodecene Using an Ionic Liquid as Solvent p-Xylene (5 g) was added to 1.67 g of 1-dodecene. The ionic liquid produced in Example 1(b) (iodide salt of 1-(2-N,N,N-dimethylpropylaminoethyl)-5-methyl-pyrrolidine-2-one; 1.8 g) containing 0.25 g of triflic acid as catalyst was added to the xylene/dodecene mixture. The two-phase system was heated to 100 degrees C. and stirred for 1 hour. GC analysis demonstrated that greater than 80% of the alkylated product was obtained, with only 20% of the dodecene un-reacted. The solution was cooled and the reaction product was decanted from the brown colored ionic liquid/acid catalyst phase. The organic phase was rapidly stirred with 30 ml of water and the acid content was determined; 0.45 g of 0.01 M NaOH was needed to neutralize the acid which is consistent with >99.8% retention of the acid in the ionic liquid (separate) phase.

The reaction produced a mixture of products as shown by GC analysis. One of the products synthesized by the reaction had the Formula:

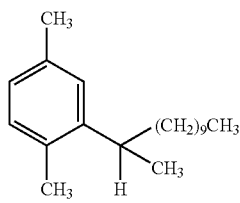

The invention claimed is:
1. A compound of the Formula:

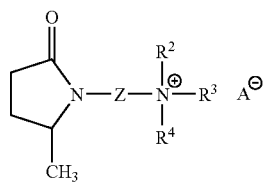

wherein:
(i) Z is —$(CH_2)_n$—, wherein n is an integer from 2 to 12;
(ii) $R^2$, $R^3$ and $R^4$ taken independently are H, —$CH_3$, —$CH_2CH_3$ or $C_3$ to $C_6$ straight-chain or branched monovalent alkyl; and
(iii) $A^-$ is an anion selected from the group consisting of $[BF_4]^-$, $[PF_6]^-$, $[SbF_6]^-$, $[CH_3CO_2]^-$, $[HSO_4]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[AlCl_4]^-$, $[CF_3CO_2]^-$, $[NO_3]^-$, $[SO_4]^{2-}$, $Cl^-$, $Br^-$, $I^-$, and $F^-$.

2. The compound of claim 1 wherein Z is —$(CH_2)_n$—, wherein n is an integer from 2 to 6.

3. The compound of claim 1 wherein the anion is $[PF_6]^-$, $[HCF_2CF_2SO_3]^-$, $[CF_3HFCCF_2SO_3]^-$, $[HCClFCF_2SO_3]^-$ or $[(CF_3SO_2)_2N]^-$.

4. The compound of claim 2 wherein the anion is $[PF_5]^-$, $[HCF_2CF_2SO_3]^-$, $[CF_3HFCCF_2SO_3]^-$, $[HCClFCF_2SO_3]^-$ or $[(CF_3SO_2)_2N]^-$.

* * * * *